(12) United States Patent
Rottmann et al.

(10) Patent No.: US 10,036,720 B2
(45) Date of Patent: Jul. 31, 2018

(54) SENSOR ELEMENT HAVING A CONDUCTOR AND LEADTHROUGH

(71) Applicant: Robert Bosch GmbH, Stuttgart (DE)

(72) Inventors: Andreas Rottmann, Strettfeld (DE); Frank Buse, Stuttgart (DE); Jens Schneider, Leonberg (DE); Thomas Juestel, Hirschaid-Juliushof (DE)

(73) Assignee: ROBERT BOSCH GMBH, Stuttgart (DE)

( * ) Notice: Subject to any disclaimer, the term of this patent is extended or adjusted under 35 U.S.C. 154(b) by 163 days.

(21) Appl. No.: 14/900,471

(22) PCT Filed: Mar. 13, 2014

(86) PCT No.: PCT/EP2014/055007
§ 371 (c)(1),
(2) Date: Dec. 21, 2015

(87) PCT Pub. No.: WO2014/202245
PCT Pub. Date: Dec. 24, 2014

(65) Prior Publication Data
US 2016/0161442 A1 Jun. 9, 2016

(30) Foreign Application Priority Data

Jun. 21, 2013 (DE) ........................ 10 2013 211 796

(51) Int. Cl.
*G01N 27/407* (2006.01)
*G01N 27/406* (2006.01)

(52) U.S. Cl.
CPC ....... *G01N 27/407* (2013.01); *G01N 27/4067* (2013.01); *G01N 27/4071* (2013.01)

(58) Field of Classification Search
CPC ............. G01N 27/4067; G01N 27/407; G01N 27/4071

(Continued)

(56) References Cited

U.S. PATENT DOCUMENTS 5,142,266 A * 8/1992 Friese .................... G01K 7/223
338/22 R
6,136,170 A 10/2000 Inoue et al.
(Continued)

FOREIGN PATENT DOCUMENTS

CN 2 033 054 2/1989
DE 197 00 700 7/1998
(Continued)

OTHER PUBLICATIONS

International Search Report for PCT/EP2014/055007, dated May 8, 2014.

*Primary Examiner* — Randy Gibson
*Assistant Examiner* — Gedeon M Kidanu
(74) *Attorney, Agent, or Firm* — Norton Rose Fulbright US LLP; Gerard Messina (57) ABSTRACT

A sensor element for detecting a physical property of a gas includes: a first end region and a second end region opposing one another; a functional element in the first end region interior that is electroconductively connected to a contact area disposed in the second end region exterior; the electrically conductive connection between the functional element and the contact area having a conductor in the interior of the sensor element essentially extending in the longitudinal direction, and having a leadthrough that essentially extends orthogonally to the longitudinal direction of the sensor element. The ratio between an electrical resistance of the conductor and an electrical resistance of the leadthrough is between 3 and 1/3.

10 Claims, 6 Drawing Sheets

(58) Field of Classification Search
USPC ........................................................ 73/23.31
See application file for complete search history.

(56) References Cited

U.S. PATENT DOCUMENTS

| | | | | |
|---|---|---|---|---|
| 2002/0112958 | A1* | 8/2002 | Diehl | G01N 27/4071 |
| | | | | 204/426 |
| 2005/0145492 | A1* | 7/2005 | Strohmaier | G01N 27/419 |
| | | | | 204/424 |
| 2005/0252770 | A1* | 11/2005 | Naito | G01N 27/4071 |
| | | | | 204/424 |
| 2007/0108047 | A1 | 5/2007 | Chang et al. | |
| 2007/0245803 | A1* | 10/2007 | Tan | G01N 27/4077 |
| | | | | 73/31.05 |
| 2010/0000293 | A1 | 1/2010 | Kawai et al. | |
| 2011/0139618 | A1* | 6/2011 | Serrels | G01N 27/4071 |
| | | | | 204/408 |
| 2012/0111726 | A1 | 5/2012 | Couto Petri et al. | |

FOREIGN PATENT DOCUMENTS

| | | | |
|---|---|---|---|
| DE | 10 2004 044 328 | | 3/2006 |
| DE | 10 2006 055797 | | 5/2008 |
| DE | 102006055797 A1 * | 5/2008 | ......... G01N 27/4071 |
| DE | 10 2012 214 133 | | 2/2013 |
| WO | WO 2005/059535 | | 6/2005 |
| WO | 2011153523 A1 | | 12/2011 |

\* cited by examiner

SENSOR ELEMENT HAVING A CONDUCTOR AND LEADTHROUGH

BACKGROUND OF THE INVENTION

1. Field of the Invention

The present invention relates to known sensor elements that serve as exhaust-gas sensors, for example, in particular as lambda probes that are widely used in motor vehicles. However, the present invention can also be applied to other types of sensor elements, for example, to sensors for detecting other gaseous components of exhaust gases, and also to particle sensors or the like. In particular, the present invention relates to a sintered or sinterable ceramic sensor element that is produced, for example, by assembling individual, in some instances imprinted ceramic green films, in particular by stacking them one upon the other.

2. Description of the Related Art

In particular, the sensor element of the type described above includes at least one electrical, electrochemical and/or electronic functional element in a first end region of the sensor element, generally a first end region facing the exhaust gas. The sensor element's ability to be electrically powered is provided here by a contact area on the outer surface thereof in a second region, typically one facing away from the exhaust gas.

The sensor element's ability to be electrically powered is provided here by an electrical connection of the functional element with the contact area that includes a conductor in the interior of the sensor element that essentially extends in the longitudinal direction of the sensor element and a leadthrough that essentially extends orthogonally to the longitudinal direction of the sensor element, in particular in the vertical direction. Sensor elements of this kind are known, for example, from the German Patent Application DE 10 2006 055 797 A1.

During operation and manufacture of the sensor element, high temperature and chemical resistances are required for the electrical connection. Therefore, noble metals, such as platinum or the like, are widely used. Since such noble metals are relatively expensive, efforts are generally directed to reducing the quantity of material used.

This type of miniaturization of the electrical connection is limited in that, at a specified resistance, the total resistance is all the greater, the smaller the particular lead cross sections are. Resulting voltage drops, respectively power losses and/or signal distortions can only be tolerated within predefined limits.

In particular, such a total resistance limit of this electrical connection of the functional element, in particular of a heating resistor, with the contact area is to be seen within the range here of 1 to 4 ohms at 20° C., in particular within the range of 2 to 3 ohms at 20° C.

BRIEF SUMMARY OF THE INVENTION

On the other hand, inventive sensor elements according to the present invention have the advantage that the quantity of material, for example, of the noble metal used for electrically connecting the functional element to the contact area, may be minimized without exceeding a definable total resistance of the electrical connection.

Underlying the present invention in the first instance is the consideration that the conductor and the leadthrough are two serially connected sections of the electrical connection. The total resistance of the electrical connection is thus cumulatively derived from the individual resistances. Secondly, underlying the present invention is the consideration that, when the conductive structures are reduced in cross section, the electrical resistance thereof is approximately inversely proportional to the quantity of material used.

Consequently, a simultaneous optimization of the total resistance of the electrical connection and of the material quantity required for the electrical connection is recognized as present when the ratio between the electrical resistance of the conductor and the electrical resistance of the leadthrough is not greater than 3 and not smaller than 1/3.

In the case of a different ratio, the material quantity that is altogether required or that is smaller for the section would be disproportionately increased, without the total resistance being significantly reduced.

Inasmuch as the specific resistance of the materials used is temperature-dependent, it is particularly necessary to assess temperature distributions that occur, respectively that can typically occur during operation of the sensor. Besides a homogeneous temperature distribution, for example, 20° C., which, for example, represents the state at initial start-up of the sensor, the present invention may also be alternatively or additionally realized with respect to inhomogeneous temperature distributions. For example, uniform increases in temperature in the longitudinal direction of 750° C. or even of 1100° C. in the area of the functional element, and of 200° C., 300° C. or even of 400° C. in the area of the leadthrough may each be used as a basis in the resulting combinations. Such temperature distributions exist, for example, on the completely heated sensor, for example, in continuous operation.

Even at different temperatures and temperature distributions, the electrical resistances of the conductors and leadthroughs are readily available to one skilled in the art, for example, by performing measurements. Also, he/she is easily able to selectively adapt the resistances, for example, by modifying the lead cross sections.

In particular, the present invention also relates to a sensor element where an electrical connection of the functional element, in particular of a heating resistor with a contact area, has already been miniaturized. In this case, the electrical resistance of the electrical connection of the functional element, in particular of the heating resistor with the contact area, is within the range of 1 to 4 ohms at 20° C., in particular within the range of 2 to 3 ohms at 20° C.

Within the scope of this application, the terms "longitudinal direction" "transverse direction," and "vertical direction" are generally merely used in the sense of a rectangular reference system. Moreover, directions may, in particular, be concerned that are characterized by the sensor element. Namely in the case of a cuboidal sensor element, for example, the longitudinal direction may be the direction in which the longest lateral edges of the sensor element point; the vertical direction may be the direction in which the shortest lateral edges of the sensor element point; and/or the transverse direction may be the direction in which the medium-length lateral edges of the sensor element point. For example, in the case of a rod-shaped sensor element, the longitudinal direction may point in the direction of an axis about which the rod-shaped sensor element is axially symmetric, respectively essentially axially symmetric.

Where reference is essentially made to only one direction, besides the direction in the narrow sense, directions also come under consideration that deviate slightly from this direction, for example, by not more than 15° and/or directions that are at least not orthogonal to this direction. Additionally, a direction is also realized by a structure essentially when the structure in question deviates in only one small portion, for example, by not more than 10% of the structure.

Within the scope of this application, "length of the sensor element" is understood to be the longitudinal extent of the sensor element; "width of the sensor element" is understood to be the transverse extent of the sensor element; and "height of the sensor element" is understood to be the vertical extent of the sensor element. This direction is also consequential for the plan view of the sensor element.

Within the scope of this application and with reference to a longitudinal direction, the term "end region of the sensor element" is generally understood to be merely a cohesive portion of the sensor element that includes the particular end of the sensor and does not represent more than 50% of the length of the sensor element. In this respect, one end region and one opposite end region overlap merely in one area, for example. "Somewhat limited" may be understood as an end region of the sensor element, in particular also as a cohesive portion of the sensor element that includes the particular end of the sensor and no longer represents one third or even no longer one fourth of the length of the sensor element.

In the present case, the term "functional element" is generally not to be narrowly interpreted. For example, it may be a question of a noble metal electrode or cermet electrode that communicates with the exterior of the sensor element and/or of an electrical resistance heater that, in particular, has an electrical resistance of maximally 30 ohms at 20° C. and/or the like.

If the resistance heater is a functional element, two electrical connections of the specific embodiments described here may be provided adjacently, in particular mirror symmetrically.

Advantageous embodiments of the present invention provide that the ratio between the electrical resistance of the conductor and the electrical resistance of the leadthrough be limited to an even greater extent within the range of 1. The electrical resistance of the conductor and the electrical resistance of the leadthrough are then equal or at least approximately equal, for example, with a ratio within the range of 2 to 1/2 or within the range of 3/2 to 2/3 or within the range of 110% to 90%.

One further refinement of the present invention, which is especially beneficial from a production engineering standpoint, is provided in that, at the end thereof facing away from the end region of the sensor element, the conductor is laterally angled, the conductor extending off-center, in particular in the transverse direction of the sensor element and, at the end thereof facing away from end region (201) of the sensor element, is angled toward the outer face of the sensor element. Two conductors of this kind may also be provided that are disposed in opposition to one another, in particular symmetrically, in particular off-center in the transverse direction of the sensor element and, at the end thereof facing away from the end region of the sensor element, are angled toward the particular outer face of the sensor element. The advantage of these specific embodiments is that, in the transverse direction, the conductor may extend relatively centrally in that, in one region of the sensor element, it may be manufactured very reliably. On the other hand, the leadthroughs must not fall below a certain minimum mutual distance since, otherwise, the breaking strength of the sensor element, in particular, would be reduced. Overall, therefore, the amount of material used and the functionality may be thereby further optimized.

In special specific embodiments of the present invention, the leadthrough is made of a conductive coating of the radial wall of a plated-through hole of the sensor element or of a conductive filling of a plated-through hole of the sensor element.

Additionally or alternatively, the conductor may include a lead and a collar, the lead or an end region of the lead facing away from the exhaust gas having, in particular, a constant or an essentially constant lead width B and being routed from the functional element into the region of the leadthrough; and, in a plan view of the sensor element, the collar being annularly disposed, in particular, around the plated-through hole, and effecting the electrical connection between the leadthrough and the lead; the annular ring having an annular ring width b, measured radially in a plan view of the plated-through hole.

In particular, the functional element may be an electrical resistance heater that, in particular, has an electrical resistance of maximally 30 ohms at 20° C. In this case, during operation, the electrical connection is a conductor of substantial currents. To avoid unwanted losses, respectively waste heat, adequate dimensioning is to be provided, in particular of the lead of the conductor that is directly adjacent to the resistance heater. On the other hand, the region of the collar may be more sparingly designed. In particular, an optimization has revealed that a width ratio, annular ring width divided by the lead width, resides within the range of from 0.1 to 0.4, preferably within the range of from 0.22 to 0.32. Overall, therefore, the quantity of material used and the functionality may be thereby further optimized.

The selection of this width ratio is, in fact, not only to be exclusively seen in synergic cooperation. Accordingly, the following is an alternative object of the present invention to which the further embodiments discussed in other respects may nevertheless be applied:

A sensor element, in particular for detecting a physical property of a gas, in particular for detecting the concentration of a gas component or the temperature or a solid component or a liquid component of an exhaust gas of a combustion engine; in the longitudinal direction thereof, the sensor element having a first end region and second end region that oppose one another; in the first end region, the sensor element, in the interior thereof, having a functional element that is electroconductively connected to a contact area disposed in the second end region on the outer face of the sensor element; the electrically conductive connection between the functional element and the contact area having a conductor in the interior of the sensor element that essentially extends in the longitudinal direction and having a leadthrough that essentially extends orthogonally to the longitudinal direction of the sensor element; the leadthrough being made of a conductive coating of the radial wall of a plated-through hole of the sensor element or of a conductive filling of the plated-through hole, and the conductor including a lead and a collar; the lead or an end region of the lead facing away from the exhaust gas having a constant or an essentially constant lead width B and being routed from the functional element into the region of the leadthrough; and, in a plan view of the sensor element, the collar being annularly disposed around the plated-through hole and effecting the electrical connection between the leadthrough and the lead; the annular ring having a width b, measured radially in a plan view of the plated-through hole; the functional element being an electrical resistance heater, which, in particular, has an electrical resistance of maximally 30 ohms at 20° C. and a width ratio, annular ring width b divided by lead width B, within the range of from 0.1 to 0.4, preferably within the range of from 0.22 to 0.32.

In particular, the diameter of the plated-through hole plus twice the annular ring width may be identical or approximately identical to the lead width. At the end thereof in the area of the leadthrough, the conductor is then not made thicker by the collar, so that material is saved without causing any appreciable functional disadvantages.

In particular, in the case of a sintered sensor element, lead width B may reside within the range of from 0.72 to 1.12 mm; and/or annular ring width b may be within the range of from 0.2 to 0.28 mm; and/or the diameter of plated-through hole D may be within the range of from 0.4 to 0.56 mm. For unsintered sensor elements, dimensions are to be added that are 25% larger in each case than those indicated for sintered sensor elements.

In particular, the functional element may be a cermet electrode having a flat design that communicates, in particular, with the exterior of the sensor element.

In this case, the electrical connection is only traversed during operation by the flow of low currents. To economize material, the lead of the conductor may be realized with a relatively small width. On the other hand, it is not possible for the region of the collar and of the leadthrough to be similarly scaled, since, otherwise, a reliable contacting would no longer be feasible under all circumstances from a standpoint of production engineering. In particular, an optimization has revealed that a width ratio—the annular ring width divided by the lead width—resides within the range of from 0.6 to 1.08, preferably with the range of from 0.7 to 0.9.

Overall, therefore, the amount of material used and the functionality may be thereby further optimized.

The selection of this width ratio is, in fact, not only to be exclusively seen in synergic cooperation. Accordingly, the following is an alternative object of the present invention to which the further embodiments discussed in other respects may nevertheless be applied:

A sensor element, in particular for detecting a physical property of a gas, in particular for detecting the concentration of a gas component or the temperature or a solid component or a liquid component of an exhaust gas of a combustion engine; in the longitudinal direction thereof, the sensor element having a first end region and a second end region that oppose one another; outside of the second end region, in particular in the first end region, the sensor element, in the interior thereof, having a functional element that is electroconductively connected to a contact area disposed in the second end region on the outer face of the sensor element; the electrically conductive connection between the functional element and the contact area having a conductor in the interior of the sensor element that essentially extends in the longitudinal direction and has a leadthrough that essentially extends orthogonally to the longitudinal direction of the sensor element; the leadthrough being made of a conductive coating of the radial wall of a plated-through hole of the sensor element or of a conductive filling of the plated-through hole, and the conductor including a lead and a collar; the lead or an end region of the lead facing away from the exhaust gas having a constant or an essentially constant lead width B and being routed from the functional element into the region of the leadthrough; and, in a plan view of the sensor element, the collar being annularly disposed around the plated-through hole and effecting the electrical connection between the leadthrough and the lead; the annular ring having a width b, measured radially in a plan view of the plated-through hole; the functional element being a cermet electrode having a flat design that communicates, in particular, with the exterior of the sensor element, and a width ratio, annular ring width b divided by lead width B within the range of from 0.6 to 1.08, preferably within the range of from 0.7 to 0.9.

In particular, in the case of a sintered sensor element, lead width B may reside within the range of from 0.3 to 0.6 mm; and/or annular ring width b may be within the range of from 0.22 to 0.36 mm; and/or the diameter of plated-through hole D may be within the range of from 0.4 to 0.56 mm. For unsintered sensor elements, dimensions are to be added that are 25% larger in each case than those indicated for sintered sensor elements.

In the context of the present invention, it may still be expedient for specific material to be selected for conductors, leads, leadthroughs and contact areas. Materials may be generally preferred here having a noble metal content of 83% by weight or more, making it possible for predefined ohmic resistances to be achieved with a minimized noble metal application. Noble metal contents of 95% by weight or more, for example, 98% by weight are even preferred for at least one lead to the heating device. A content of at least 1% by weight of Al2O3, optimally of even at least 1.5% by weight of Al2O3, preferably of maximally 2.5% by weight of Al2O3, turns out to be beneficial for precise adjustability of the electrical resistance of these structures. At least one lead to the heating device, together with the heating device, may be made in one piece and of the same material.

Additionally or alternatively, for the lead to the cermet electrode and/or for at least one contact area, a lower noble metal content than for the at least one lead to the heating device is provided, preferably, for example, of 83% by weight to 87% by weight; in particular, in the lead to the cermet electrode, a content of ZrO2 and Y2O3 of together 12% by weight to 16% by weight being provided. It is advantageous that the lead to the cermet electrode, together with the cermet electrode, may be manufactured in one process step and from the same material. An Al2O3 content, preferably 0.2% by weight to 1% by weight is also advantageous for the lead to the cermet electrode, respectively for the cermet electrode.

Additionally or alternatively, for at least one leadthrough, a lower noble metal content is provided than for the at least one lead to the heating device, preferably, for example, of 83% by weight to 87% by weight; a content of ZrO2 and Y2O3 of, together 3% by weight to 8% by weight and, additionally, a content of Nb2O5 of 6% by weight to 12% by weight being provided in the leadthrough. It is advantageous that the leadthroughs are able to be more effectively handled during the manufacturing process. In particular, appropriate compounds have more effective rheologic properties and make possible a more effective ceramic binding of the leadthroughs within the sensor elements. Moreover, in connection with sensor elements that are predominantly composed of YSZ, a reduced oxygen ion conductivity thereby results in the peripheral regions of the leadthroughs, which improves the functionality of the sensor elements.

The noble metal contents mentioned above may, in particular, be made of platinum. Alternatively, in particular relative to at least one leadthrough, contents, preferably 0.2% by weight to 0.8% by weight, relative to the total composition of the materials, may be made of rhodium to stabilize the metal phase; and/or contents, preferably 0.2% by weight to 1% by weight, relative to the total composition of the materials, may be made of palladium.

Other noble metal contents may always be provided.

DETAILED DESCRIPTION OF THE INVENTION

Figure 1:
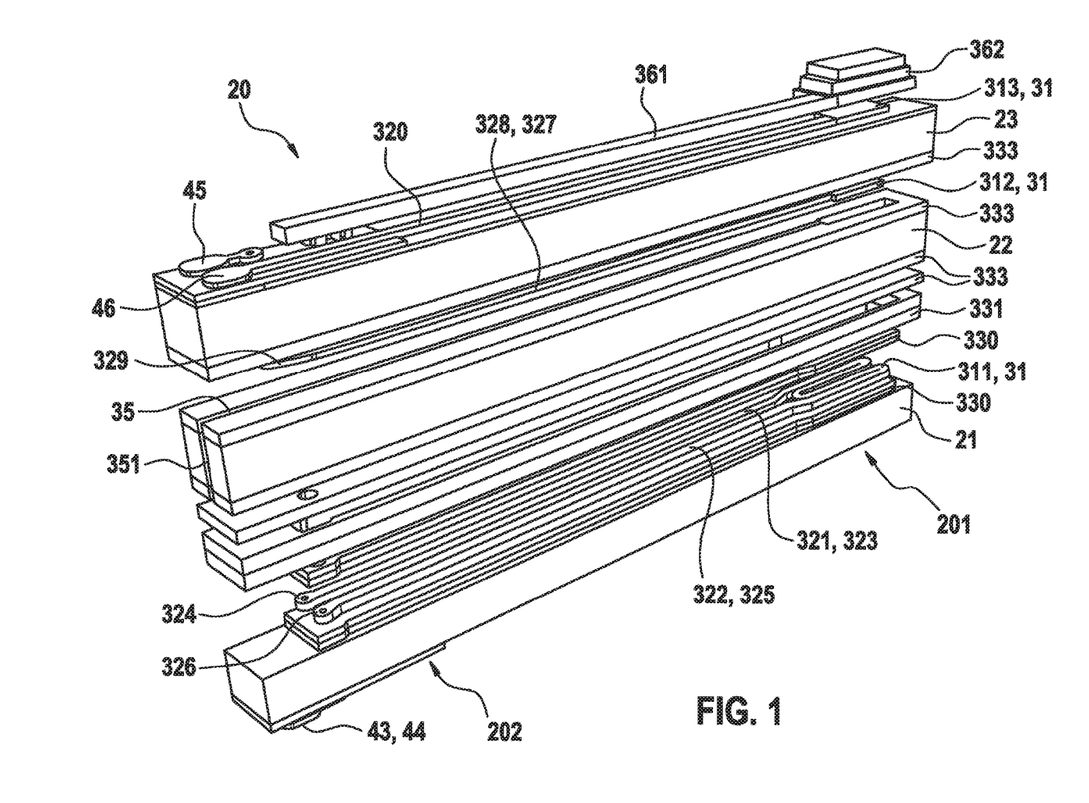
FIG. 1 shows a sensor element according to the present invention.

As an exemplary embodiment of the present invention, FIG. 1 shows an overall view of a sensor element 20, which may be mounted in a housing of a gas sensor (not shown) that is used for determining the oxygen concentration in an exhaust gas of a combustion engine (not shown). If appropriate functional elements are provided, it is self-evident that the present invention is also suited for other sensors, such as sensors used for measuring particulate matter.

In FIG. 1, the sensor element extends in the longitudinal direction from left to right, a first end region 201 of sensor element 20 being shown on the right, and a second end region 202 of sensor element 20 on the left. If sensor element 20 is installed and operated as intended, first end region 201 thereof faces an exhaust gas, and second end region 202 thereof faces away from the exhaust gas.

In addition, in FIG. 1, sensor element 20 extends in the transverse direction from front to back and in the vertical direction from bottom to top.

Sensor element 20 is assembled from imprinted ceramic layers that are formed in this example as a first, second and third solid electrolyte foil 21, 22, 23 and contain yttrium-oxide stabilized zirconium oxide (YSZ). In the example, prior to a sintering process, solid electrolyte foils 21, 22, 23 have a length of 72 mm, a width of 5 mm, and a height of 540 μm. Foils of a sintered sensor element 20 have edge lengths diminished by 20%.

Figure 3:
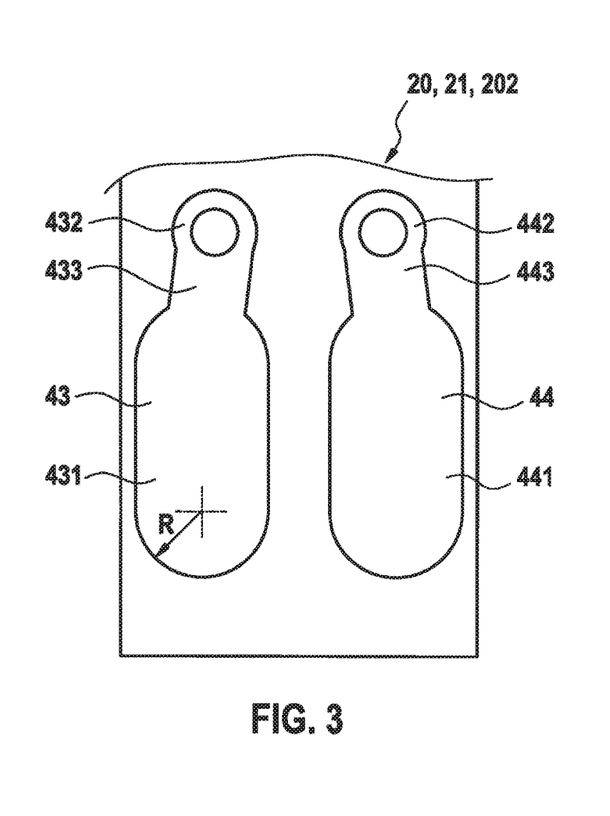
FIG. 3 shows second end region 202 of sensor element 20 facing away from the exhaust gas in a bottom view below first solid electrolyte foil 21 pointing downwardly in FIG. 1.

On the large surface area thereof that is outwardly pointing from sensor element 20, on the bottom of FIG. 1, first solid electrolyte foil 21 is provided in second end region 202 of sensor element 20 with a contact area 43 and a further contact area 44, here imprinted; see also FIG. 3.

On the large surface area thereof, pointing inwardly from sensor element 20, in the top of FIG. 1, first solid electrolyte foil 21 is provided in first end region 201 of sensor element 20 with a meander-shaped heating device 311 as a functional element 31 that is used for heating first end region 201 of sensor element 20. In a continuation of meander-shaped heating device 311, a conductor 321, 322 is connected in each case at the ends thereof, the transition from heating device 311 to conductor 321, 322 being characterized by an increase of the structure width and/or height, respectively by a decrease in the electrical resistance per length.

On the exhaust gas side, conductors 321, 322 have a section denoted as lead 323, 325, which, in the present case, has a constant width. In addition, facing away from the exhaust gas, conductors 321, 322 have a section denoted as a collar 324, 326, which is annular here; see also FIG. 4.

On the large surface area thereof that points inwardly from sensor element 20, on the top of FIG. 1, first solid electrolyte foil 21 is also provided with insulation layers 330 and a sealing frame 331, as well as with a foil binder layer 333, in this case imprinted.

Figure 6:
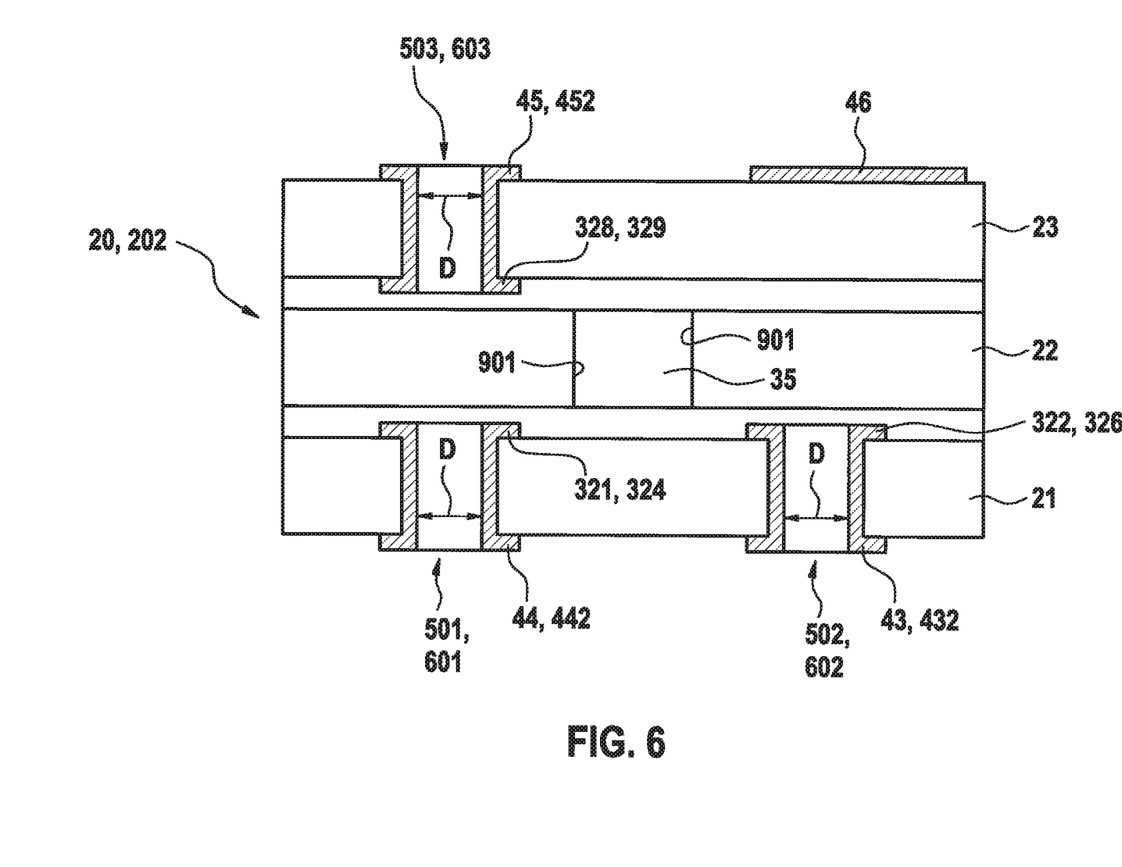
FIG. 6 shows, purely schematically, a sectional view through sensor element 20 shown in preceding FIG. 1 through 5, in a plane perpendicular to the longitudinal direction of sensor element 20 through leadthroughs 501, 502, 503.

In second end region 202, first solid electrolyte foil 21 has two leadthroughs 501, 502 that extend orthogonally through first solid electrolyte foil 21 and, in each case, electroconductively connect a contact area 43, 44 to a collar 324, 326 of a conductor 321, 322; see FIG. 6.

Second solid electrolyte foil 22 is provided on each of both sides with a foil binder layer 333; in addition, second solid electrolyte foil 22 features a reference gas channel 35 that extends along a reference gas channel 351, which faces away from the exhaust gas, into first end region 201 of sensor element 20, and thereby extends centrally in the transverse direction. Reference gas channel 35 is configured to be unfilled; in particular no porous fillings are provided therein.

At the bottom in FIG. 1, opposite reference gas channel 35, on large surface area thereof, which is inwardly pointing from the point of view of sensor element 20, third solid electrolyte foil 23 is provided with a cermet electrode 312 as a functional element 31 for measuring an oxygen concentration. In a continuation of cermet electrode 312, a conductor 328 is connected at the end thereof, the transition from the cermet electrode to conductor 328 is characterized by a decrease in the structure width.

On the exhaust gas side, conductor 328 has a section denoted as lead 327, which has a constant width here. In addition, facing away from the exhaust gas, conductor 328 features a section denoted as a collar 329, which is annular here; see also FIG. 5. Provided on this side of third solid electrolyte layer 23, at least where otherwise unprinted, is a foil binder layer 333.

Figure 2:
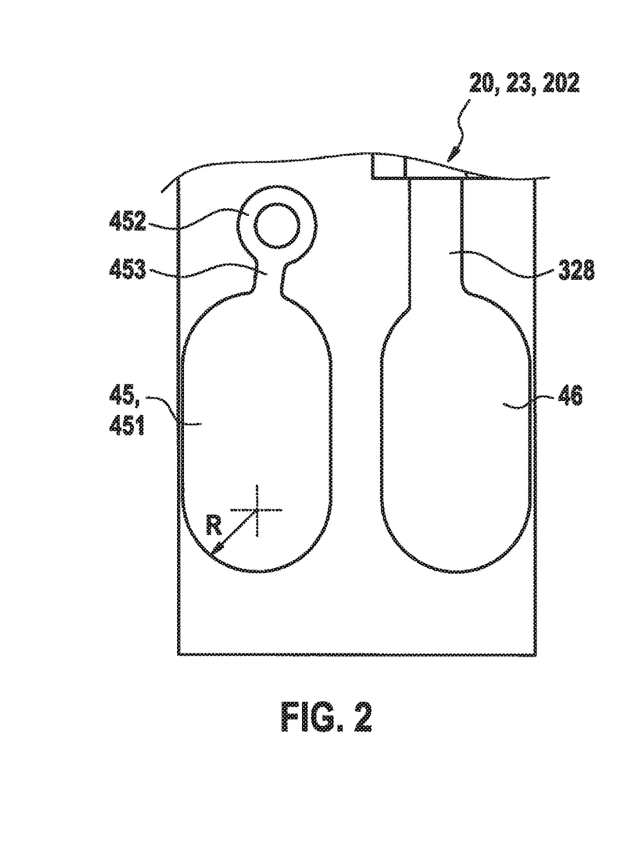
FIG. 2 shows, in a plan view of third solid electrolyte foil 23, a second end region 202 of sensor element 20 facing away from the exhaust gas.

At the top of FIG. 1, on the large surface area thereof that points outwardly from sensor element 20, third solid electrolyte foil 23 is provided in second end region 202 of sensor element 20 with a contact area 45 and a further contact area 46, here imprinted; see also FIG. 2.

Adjoining further contact area 46 is a conductor 320 having a constant width, for example, that extends to a further cermet electrode 313 disposed in first end region 201 of sensor element 20. Conductor 320 is covered with a, for example, impervious cover layer 361; further cermet electrode 313 is provided with porous layers 362, thereby ensuring a communication between the exterior and further cermet electrode 313.

In the second end region, third solid electrolyte foil 23 features a leadthrough 503 that extends orthogonally through third solid electrolyte foil 23 and electroconductively connects contact area 45 with collar 329; see FIG. 6.

In a plan view of third solid electrolyte foil 23, FIG. 2 shows second end region 202 of sensor element 20 facing away from the exhaust gas. From a perspective there of first end region 201 of sensor element 20 facing the exhaust gas, contact area 45 is configured to the left.

Contact area 45 is composed of three portions, namely of a trunk portion 451, a head portion 452, and of a neck portion 453. Trunk portion 451 is disposed on the side of contact area 45 facing away from the exhaust gas. It has a basic oblong form that results from a rectangle of the same length and width by a maximum rounding of the corners, thus by a rounding with a radius of curvature R that corresponds to half of the width of trunk portion 451, respectively of contact area 45. Thus, in this manner, semi-circular end regions of trunk portion 451, respectively of contact area 45 are formed on the side of contact area 45 facing away from the exhaust gas.

Relative to an unsintered sensor element 20 (sintered: −20%), the length of trunk portion 451 in this example is 2.5 mm or more; the width of trunk portion 451 is 1.5 mm or more. Trunk portion 451 is spaced apart from the left outer edge of sensor element 20 by 0.4 mm or less and from the front outer edge of sensor element 20 by 1.3 mm or less.

Head portion 452 is disposed on the side of contact area 45 facing the exhaust gas. Head portion 452 is annular, for example, having an inner diameter of 0.5 mm or less and an outer diameter of 1 mm or more, relative to an unsintered sensor element 20 (sintered: −20%).

Neck portion 453 is configured between trunk portion 451 and head portion 452. In comparison with trunk portion 451 and head portion 452, it forms a constricted region of contact area 45 having a minimal width of 0.3 mm in the example and a length of 0.3 mm relative to an unsintered sensor element 20 (sintered: −20%).

In the example, trunk portion 451 features a mirror symmetry relative to an axis that points in the longitudinal direction of sensor element 20. Head portion 452 and neck portion 453 likewise have a mirror symmetry; however, relative to an axis that is rotated relative to the longitudinal axis of sensor element 20 by 9° in a plan view of sensor element 20 in the mathematically negative direction of rotation, so that head portion 452 and neck portion 453 are altogether slightly tilted toward the middle of the sensor.

Head portion 452 of contact area 45 cooperates electroconductively together with a leadthrough 503 through third solid electrolyte layer 23.

Moreover, from a perspective of first end region 201 of sensor element 20 facing the exhaust gas, further contact area 46 is configured to the right next to contact area 45 in FIG. 2. In this sense, thus transposing left and right, the configuration and size of further contact area 46 correspond to that of trunk portion 451 of contact area 45 under the condition that there be a spacing of at least 0.6 mm, relative to an unsintered sensor element 20 (sintered: −20%) between contact area 45 and further contact area 46.

Further contact area 46 is merely composed of a portion corresponding to trunk portion 451 of contact area 45, thus has neither a head portion nor a neck portion. It also does not cooperate with a leadthrough; instead, it is directly contacted by conductor 328 that leads to further cermet electrode 313. Relative to a central axis of further contact area 46, a central axis of conductor 328 is transversely inwardly offset, in the longitudinal direction by 0.1 mm to 0.4 mm, in the example by 0.2 mm, relative to an unsintered sensor element 20 (sintered: −20%).

Contact areas 45, 46 have a noble metal content of 83% by weight to 87% by weight, and a content of ZrO2 and Y2O3, together, of 12% by weight to 16% by weight.

FIG. 3 shows second end region 202 of sensor element 20 facing away from the exhaust gas in a bottom view below first solid electrolyte foil 21 pointing downwardly in FIG. 1. From a perspective there of first end region 201 of sensor element 20 facing the exhaust gas, contact area 43 is configured there to the left.

Contact area 43 is composed of three portions, namely of a trunk portion 431, a head portion 432, and of a neck portion 433. Trunk portion 431 is disposed on the side of contact area 43 facing away from the exhaust gas. It has a basic oblong form that results from a rectangle of the same length and width by a maximum rounding of the corners, thus by a rounding with a radius of curvature R that corresponds to half of the width of trunk portion 431, respectively of contact area 43. Thus, in this manner, semi-circular end regions of trunk portion 431, respectively of contact area 43 are formed on the side of contact area 43 facing away from the exhaust gas.

Relative to an unsintered sensor element 20 (sintered: −20%), the length of trunk portion 431 in this example is 2.5 mm or more; the width of trunk portion 431 is 1.5 mm or more. Trunk portion 431 is spaced apart from the left outer edge of sensor element 20 by 0.4 mm or less and from the front outer edge of sensor element 20 by 1.3 mm or less.

Head portion 432 is disposed on the side of contact area 43 facing the exhaust gas. Head portion 432 is configured to be annular, for example, having an inner diameter of 0.5 mm or less and an outer diameter of 1 mm or more, relative to an unsintered sensor element 20 (sintered: −20%).

Neck portion 433 is configured between trunk portion 431 and head portion 432. In comparison with trunk portion 431 and head portion 432, it forms a constricted region of contact area 43 having a minimal width of 0.9 mm in the example and a length of 0.3 mm relative to an unsintered sensor element 20 (sintered: −20%).

Neck portion 433 of contact area 43 is substantially wider, in this case larger by a factor greater than two than neck portion 451 of contact face 45 in FIG. 2. The background is that high currents are fed via contact area 43 of heating device 311, while only comparatively low currents are fed via contact area 45 of cermet electrode 312. Contact area 43 is consequently configured with a reduced ohmic resistance, respectively widened neck region 433.

In the example, trunk portion 431 features a mirror symmetry relative to an axis that points in the longitudinal direction of sensor element 20. Head portion 432 and neck portion 433 likewise have a mirror symmetry, however, relative to an axis that is rotated relative to the longitudinal axis of sensor element 20 by 9° in a plan view of sensor element 20 in the mathematically negative direction of rotation, so that head portion 432 and neck portion 433 are altogether slightly tilted toward the middle of the sensor.

Head portion 432 of contact area 43 cooperates electroconductively with a leadthrough 501 through first solid electrolyte layer 21.

Moreover, from a perspective of first end region 201 of sensor element 20 facing the exhaust gas, further contact area 44 is configured to the right next to contact area 43 in FIG. 3. In this sense, thus transposing left and right and the positive direction of rotation with the negative direction of rotation, the configuration and size of further contact area 46 correspond to the configuration and size of contact area 43 under the condition that there be a spacing of at least 0.6 mm, relative to an unsintered sensor element 20 (sintered: −20%) between contact area 43 and further contact area 44.

Contact areas 43, 44 have a noble metal content of 83% by weight to 87% by weight, and a content of ZrO2 and Y2O3, together, of 12% by weight to 16% by weight.

Figure 4:
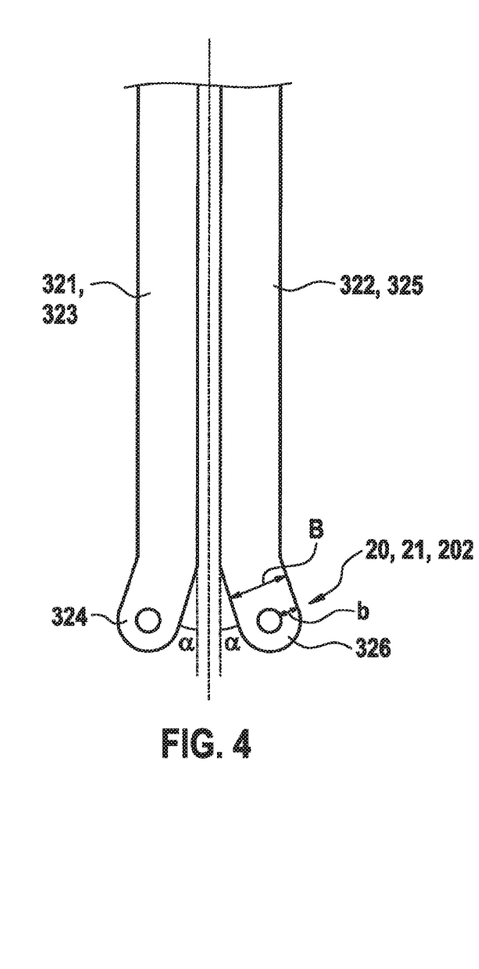
FIG. 4 shows second end region 202 of sensor element 20 facing away from the exhaust gas in a plan view of first solid electrolyte foil 21, from above in FIG. 1.

FIG. 4 shows second end region 202 of sensor element 20 facing away from the exhaust gas in a plan view of first solid electrolyte foil 21, from above in FIG. 1. From a perspective there of first end region 201 of sensor element 20 facing the exhaust gas, conductor 322 is configured to the right. Conductor 322 is composed of two portions, namely of a lead 325 and of a collar 326.

Lead 325 forms the exhaust gas-side section of conductor 322 and extends from heating device 311 on the exhaust gas-side to collar 326 that is disposed to face away from the exhaust gas side thereof. In the present case, lead 325 has a width B of 1.2 mm and extends on the exhaust gas-side at a spacing in the transverse direction of 0.25 mm to the central longitudinal axis of sensor element 20, in each case relative to an unsintered sensor element 20 (sintered: −20%). In an end region facing away from the exhaust gas, lead 325 is angled 18° to the right, thus outwardly.

Collar 326 is annular in form and, in the present case, describes an arc of 180°, whose outer diameter is identical to width B of lead 325 and whose inner diameter is 0.4 mm. In each case, relative to an unsintered sensor element 20 (sintered: −20%), a width of the collar is thus 0.3 mm. A ratio of collar width b to lead width B is 0.33.

The electrical resistance of leadthrough 501 is equal or approximately equal to that of conductor 322 relative to a temperature distribution that may, respectively may typically occur during operation of the sensor. Besides a homogeneous temperature distribution, for example, 20° C., inhomogeneous temperature distributions may also be alternatively excluded here. For example, uniform increases in temperature in the longitudinal direction of 1100° C. within the range of heating device 311 and of 200° C., 300° C. or even of 400° C. within the range of leadthrough 501 may also be used as a basis.

The electrical resistance of the electrical connection of the functional element, in particular of heating device 311 with contact area 43 is within the range of 2.5 ohms at 20° C., for example.

Moreover, in FIG. 4, from a perspective of first end region 201 of sensor element 20 facing the exhaust gas, conductor 321 is symmetrically disposed relative to the central longitudinal axis of conductor 322. In this sense, the configuration and size of conductor 321 correspond to that of conductor 322, thus, with transposition of left and right.

Leads 325, 323 feature a noble metal content of more than 95% by weight, for example, of 98% by weight and of at least 1% by weight of Al2O3.

The electrical resistance of leadthrough 502 is equal or approximately equal to that of conductor 321 relative to a temperature distribution that may, respectively may typically occur during operation of the sensor. Besides a homogeneous temperature distribution, for example, 20° C., inhomogeneous temperature distributions may also be alternatively excluded here. For example, uniform increases in temperature in the longitudinal direction of 1100° C. within the range of heating device 311 and of 200° C., 300° C. or even of 400° C. within the range of leadthrough 501 may also be used as a basis.

Figure 4A:
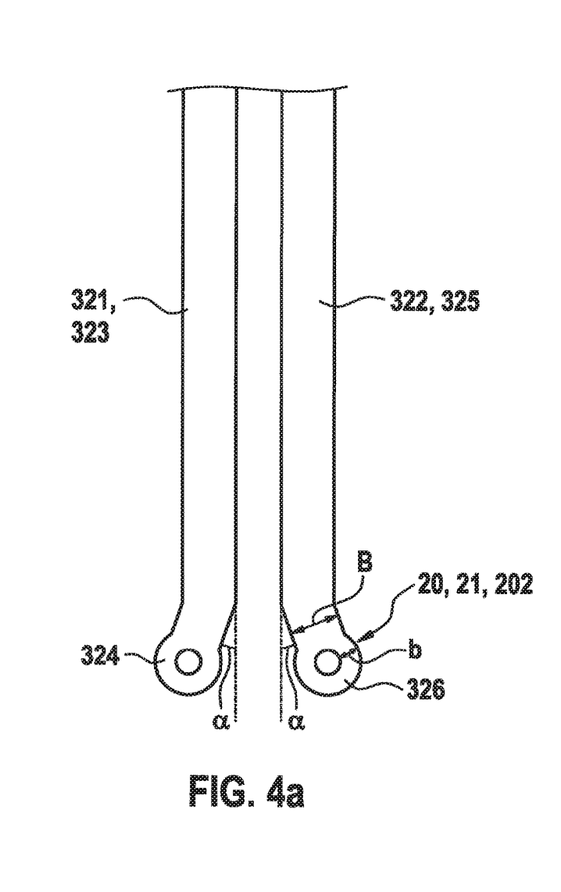
FIG. 4a shows a sensor element 20 having slightly modified leads 323, 325, in comparison to the configuration shown in FIG. 4.

As a variant, FIG. 4a shows a sensor element 20 having slightly modified leads 323, 325, the modification residing merely in that width B of leads 323, 225 is only 1.08 mm instead of 1.2 mm, thus, slightly reduced (10%) in comparison to collar 324, 326. The metric dimensions are based on an unsintered sensor element 20 (sintered: −20%).

Figure 5:
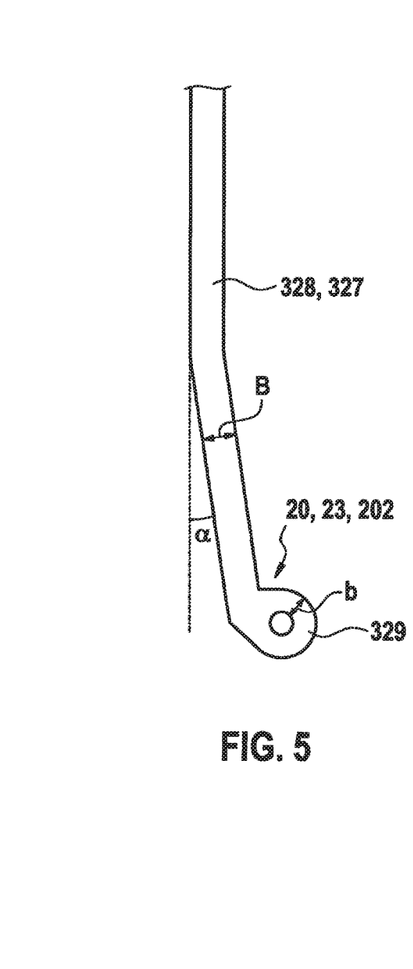
FIG. 5 shows second end region 202 of sensor element 20 facing away from the exhaust gas in a bottom view below third solid electrolyte foil 23, pointing downwardly in FIG. 3.

FIG. 5 shows second end region 202 of sensor element 20 facing away from the exhaust gas in a bottom view below third solid electrolyte foil 23, pointing downwardly in FIG. 3. From a perspective there of first end region 201 of sensor element 20 facing the exhaust gas, conductor 322 is configured to the right. Conductor 322 is composed of two portions, namely of a lead 327 and of a collar 329.

Lead 327 forms the exhaust gas-side section of the conductor and extends from cermet electrode 312 on the exhaust gas-side to collar 329 disposed to face away from the exhaust gas side of lead 327. In the present case, the lead has a width B of 0.4 mm (unsintered; sintered: −20%) and extends on the exhaust gas side in such a way that it is disposed within reference gas channel 35 in a perpendicular projection in a plan view of sensor element 20. Thus, this section of lead 327 is substantially protected from squeezing during the production process.

In an end region facing away from the exhaust gas, lead 327 is angled by not more than 25°, here 8° to the right, thus outwardly. In this end region facing away from the exhaust gas, the lead intersects with the edge 901 of reference gas channel 35 in a perpendicular projection in a plan view of sensor element 20. The comparatively small angle of intersection results in a long overlap zone between conductor 328 and the edge of reference gas channel 35 and, thus, in turn, in an effective protection against squeezing of lead 327 during the production process.

Collar 329 has an annular design. Relative to an unsintered sensor element 20 (sintered: −20%), a width of collar b is 0.3 mm. A ratio of collar width b to lead width B is 0.75.

Lead 327 has a noble metal content of 83% by weight to 87% by weight, and a content of ZrO2 and Y2O3, together, of 12% by weight to 16% by weight.

The electrical resistance of leadthrough 503 is equal or approximately equal to that of conductor 328 relative to a temperature distribution that may, respectively may typically occur during operation of the sensor. Besides a homogeneous temperature distribution, for example, 20° C., inhomogeneous temperature distributions may also be alternatively excluded here. For example, uniform increases in temperature in the longitudinal direction of 750° C. within the range of cermet electrode 312 and of 200° C., 300° C. or even of 400° C. within the range of leadthrough 503 may also be used as a basis.

Figure 5A:
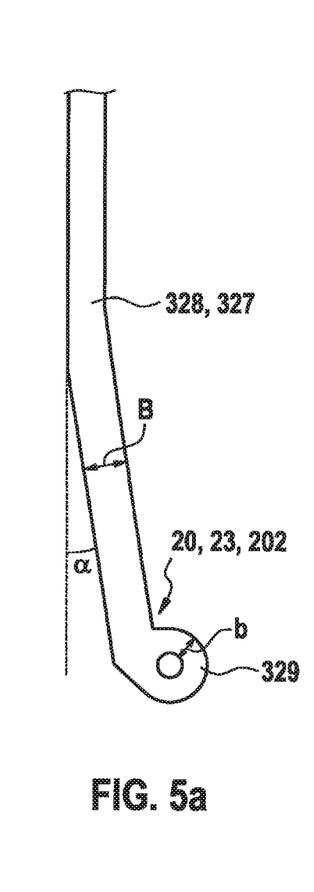
FIG. 5a shows a sensor element 20 having a slightly modified lead 328, in comparison to the configuration shown in FIG. 5.

As a variant, FIG. 5a shows a sensor element 20 having a slightly modified lead 328; the modification residing merely in that width B of lead 328 is increased in the end region facing away from the exhaust gas relative to the region of lead 328 facing the exhaust gas by 50%, by 0.4 mm to 0.6 mm. The metric dimensions are based on an unsintered sensor element 20 (sintered: −20%).

FIG. 6 shows, purely schematically, a sectional view through sensor element 20 shown in preceding FIG. 1 through 5, in a plane perpendicular to the longitudinal direction of sensor element 20 through leadthroughs 501, 502, 503.

Leadthroughs 501, 502, 503 are made as a conductive coating of the radial wall of a plated-through hole 601, 602, 603 of sensor element 20. In the example, the diameter of plated-through holes 601, 602, 603 is 0.6 mm in relation to an unsintered sensor element 20 (sintered: −20%, thus 0.48 mm).

It is readily apparent that leadthroughs 501, 502, 503, together with reference gas channel 35, are each configured to be overlap-free in a plan view of sensor element 20.

Leadthroughs 501, 502, 503 have a noble metal content of 83% by weight to 87% by weight, and a content of ZrO2 and Y2O3 of, together, 3% by weight to 8% by weight and, additionally, a content of Nb2O5 of 6% by weight and of 12% by weight.

Figure 7:
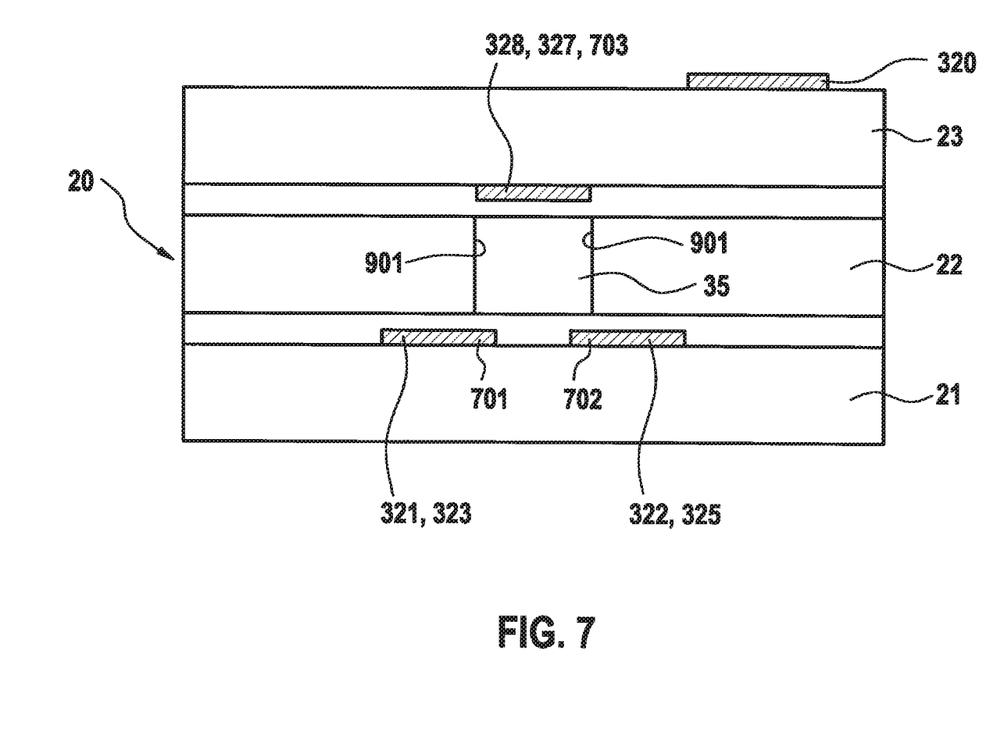
FIG. 7 shows, purely schematically, a sectional view through sensor element 20 shown in preceding FIG. 1 through 5, in a plane orthogonal to the longitudinal direction of sensor element 20 approximately in the area of half of the longitudinal extent of sensor element 20.

FIG. 7 shows, purely schematically, a sectional view through sensor element 20 shown in preceding FIG. 1 through 5, in a plane orthogonal to the longitudinal direction of sensor element 20 approximately in the area of half of the longitudinal extent of sensor element 20.

A plan view of sensor element 20 reveals that conductor 328, respectively lead 327, which is routed to cermet electrode 312, comes to overlap 703 over the full width thereof with reference channel 35. In addition, conductors 321, 322, respectively leads 323, 325, which are routed to the resistance heater, come to overlap 701, 702, in each case over approximately 10% of the width thereof, with reference channel 35.

What is claimed is:

1. A sensor element for detecting a physical property of a gas of a combustion engine, comprising:
    a first end region and a second end region opposing one another in the longitudinal direction of the sensor;
    a functional element in the interior of the first end region, the functional element being electroconductively connected to a contact area disposed in the second end region on the outer face of the sensor element;
    a conductor in the interior of the sensor element forming the electrically conductive connection between the functional element and the contact area, the conductor essentially extending in the longitudinal direction; and
    at least one leadthrough essentially extending orthogonally to the longitudinal direction of the sensor element;
    wherein the ratio between an electrical resistance of the conductor and an electrical resistance of the leadthrough is not greater than 3 and not less than 1/3,
    wherein the leadthrough is made of a conductive coating of a radial wall of a plated-through hole of the sensor element; and
    wherein the conductor includes a lead and a collar;
    wherein at least an end region of the lead facing away from the exhaust gas has an essentially constant lead width and is routed from the functional element into the region of the leadthrough;
    wherein in a plan view of the sensor element, the collar is annularly disposed around the plated-through hole and effecting the electrical connection between the leadthrough and the lead; and
    wherein the annular ring has an annular width measured radially in a plan view of the plated-through hole wherein a width ratio, defined as the annular ring width divided by the lead width, is within the range of 0.1 to 0.4.

2. The sensor element as recited in claim 1, wherein the electrical resistance of the conductor and the electrical resistance of the leadthrough are at least approximately equal.

3. The sensor element as recited in claim 1, wherein the conductor is laterally angled at an end facing away from one of the end regions of the sensor element, the conductor extending off-center in the transverse direction of the sensor element and, at the end of the conductor facing away from one of the end regions of the sensor element, being angled toward the outer face.

4. The sensor element as recited in claim 1, wherein the functional element is an electrical resistance heater having an electrical resistance of maximally 30 ohms at 20° C.

5. The sensor element as recited in claim 4, wherein a sum of a diameter of the plated-through hole plus twice the annular ring width is at least approximately identical to the lead width.

6. The sensor element as recited in claim 4, wherein:
    the lead width is within the range of 0.72 to 1.12 mm;
    the annular ring width is within the range of 0.2 to 0.28 mm; and
    the diameter of the plated-through hole is within the range of 0.4 to 0.56 mm.

7. The sensor element as recited in claim 1, wherein the functional element is a cermet electrode having a flat configuration and communicating with the exterior of the sensor element.

8. The sensor element as recited in claim 7, wherein at least one leadthrough belonging to the heating device is disposed opposite a leadthrough belonging to the cermet electrode, in a direction orthogonally to the longitudinal direction of the sensor element and orthogonally to the transverse direction of the sensor element.

9. The sensor element as recited in claim 7, wherein a width ratio, defined as the annular ring width divided by the lead width, is within the range of 0.6 to 1.08.

10. The sensor element as recited in claim 9, wherein:
    the lead width is within the range of 0.3 to 0.6 mm;
    the annular ring width is within the range of 0.22 to 0.36 mm; and
    the diameter of the plated-through hole is within the range of 0.4 to 0.56 mm.

* * * * *